US006262301B1

(12) United States Patent
Skjold et al.

(10) Patent No.: US 6,262,301 B1
(45) Date of Patent: Jul. 17, 2001

(54) PROCESS OF PREPARING A HIGH-ENERGY SOFTENING AGENT

(75) Inventors: Erlend Skjold, Sætre; Øyvind Hammer Johansen, Oslo; Richard Gjersøe, Heer; Terje Halvorsen, Røyken; Alf Berg, Sætre; Trine Granby, Haslum; Mona Christensen, Drammen, all of (NO)

(73) Assignee: Dyno Asa Forsvarsprodukter, Saerte (NO)

( * ) Notice: Subject to any disclaimer, the term of this patent is extended or adjusted under 35 U.S.C. 154(b) by 0 days.

(21) Appl. No.: 09/524,013

(22) Filed: Mar. 13, 2000

Related U.S. Application Data

(60) Provisional application No. 60/159,561, filed on Oct. 15, 1999.

(51) Int. Cl.$^7$ ................................................. C07C 243/02
(52) U.S. Cl. ........................................... 564/110; 564/111
(58) Field of Search ..................................... 564/110, 111

(56) References Cited

U.S. PATENT DOCUMENTS

| 2,485,855 | 10/1949 | Blomquist et al. . |
| 2,678,946 | 5/1954 | Blomquist et al. . |
| 5,520,757 | 5/1996 | Lutz . |

OTHER PUBLICATIONS

STN International, file CAPLUS, CAPLUS Accession No. 1998:288203, A. Lu, "Development of Nitroxyethylnitramine plasticizer", 1998.

*Primary Examiner*—Johann Richter
*Assistant Examiner*—Brian J. Davis
(74) *Attorney, Agent, or Firm*—Young & Thompson

(57) ABSTRACT

The present invention relates to a continuous process of preparing N-alkyl-nitratoethylamines and a production plant for carrying out a continuous process of preparing such N-alkyl-nitratoethylamines.

15 Claims, 1 Drawing Sheet

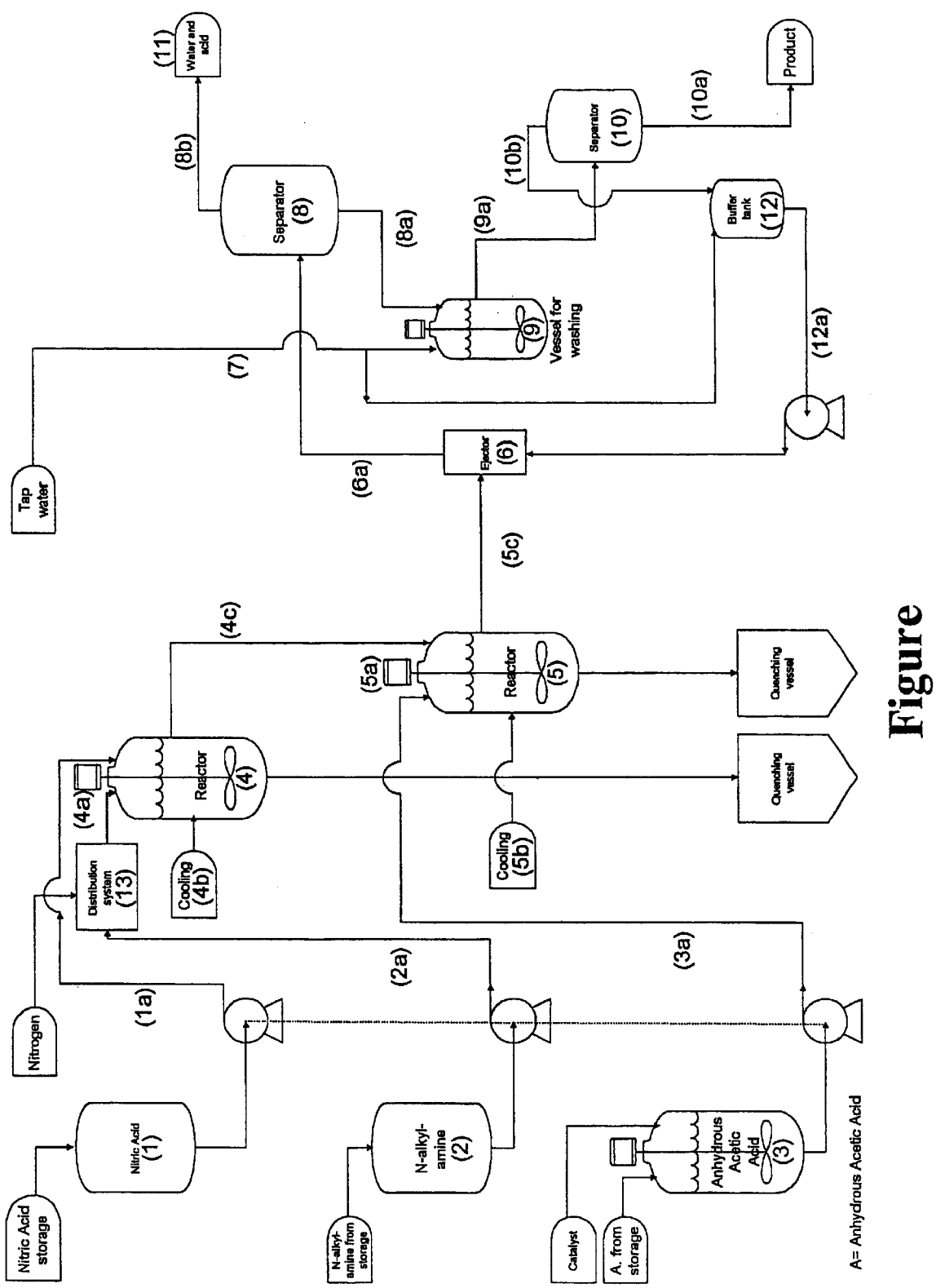
Figure

PROCESS OF PREPARING A HIGH-ENERGY SOFTENING AGENT

This application claims benefit of 60/159,561 filed Oct. 15, 1999.

FIELD OF THE INVENTION

The present invention relates to a continuous process of preparing N-alkyl-nitratoethylnitramines (or NENA-compounds), and in a particularly preferred embodiment a continuous process of preparing butyl-nitratoethylnitramine (butyl-NENA). Further, the invention relates to a plant for effecting such a continuous process.

BACKGROUND OF THE INVENTION

Nitroethylnitramines, in the field known as NENA-compounds, (nitratoethyl-nitramine), have recently been discovered to be potentially very useful ingredients in propellants and explosives (The NENA compounds constitute a large family of energetic plasticizers). This is due to an increasing demand for developing less sensitive propellants and explosive compositions. A large group of NENA-compounds are useful—methyl, ethyl, propyl, butyl etc..

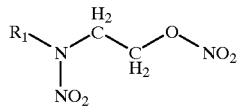

wherein $R^1$ is alkyl.

Alkyl-NENAs include a nitrate ester as well as a nitramino group, and as a consequence thereof, the NENA compounds are of high interest to both the pro-pulsion, rocket propultion, and military high explosives for low sensitivity ammunition. Alkyl-NENAs has numerous advantages as energetic materials. A well known property is the ability to readily plasticize cellulosic polymers (such as e.g. nitrocellulose) to yield a new type of double-base propellants. These double-base propellants offer very low molecule weight combustion gases (less than 20), which in turn provides for a higher driving force (impetus) at any given flame temperature than the conventional gun propellants or alternatively a lower flame temperature at any given impetus level. Alkyl-NENAs have also been demonstrated to be successful as ingredients in more modern propellant and explosive compositions, particularly as plasticizers in polymeric materials such as poly-NIMMO, HTPE and others.

PRIOR ART

Alkyl-NENAs were first discovered in the early part of the second world war (most probably in 1942) by the research scientists George Wright and Walter Chute at the University of Toronto. At the same time the US Navy was searching for a new flashless gun propellant. Alkyl-NENAs appeared to be a promising solution. The research on Alkyl-NENAs quickly spread to other laboratories in other universities. Seven U.S. patent applications were filed on the same day, Dec. 30, 1944; George Wright and Walter Chute (U.S. Pat. No. 2,461,582, U.S. Pat. No. 2,462,052), Alfred Blomquist and Fred Fiedorek (U.S. Pat. No. 2,481,283, U.S. Pat. No. 2,485,855, U.S. Pat. No. 2,678,946 and U.S. Pat. No. 2,669,576) and John Kincaid (U.S. Pat. No. 2,698,228).

In the last years particularly the interest for butyl-NENA has been increasing. By substituting butyl-NENA for NG (nitroglycerin) in propellants and explosives and thus contributing to an increased safety, this type of propellants and explosives were able to comply with the present military requirements of advanced ammunition. Butyl-NENA has improved thermochemical properties, and is in addition a particularly good nitrocellulose plasticizer. It is expected that butyl-NENA can be used as an important, energetic material.

The NENA-compounds are synthetized batch-wise in a two-step synthesis starting from commercially accessible alkylaminoethanols having a low price by using concentrated nitric acid followed by scavenging the water formed using acetic acid anhydride. By the nitration the hydroxyl group is converted to a nitrate ester group, and the amine group to a nitramine group.

Step 1

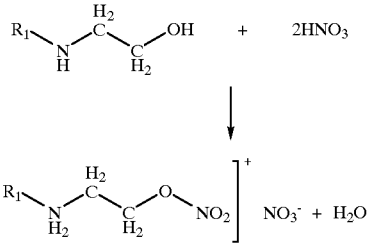

wherein $R_1$ is alkyl.

Step 2

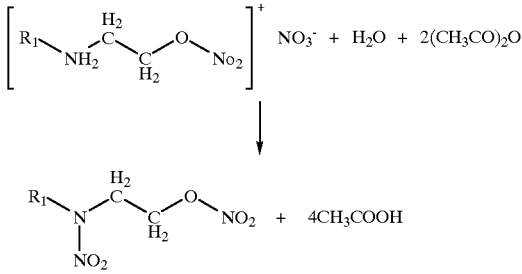

wherein $R_1$ is alkyl.

U.S. Pat. No. 2,678,946 was granted on May 18, 1954. Alfred Blomquist and Fred Fiedorek were mentioned as inventors in the patent. This patent relates to a process of preparing nitroxy alkylnitramines, in which the examples among others show the preparation of methyl-NENA (example II) and ethyl-NENA (example III). Claim 1 of said patent claims a process of preparing nitroxy alkylnitramines, wherein a secondary amine reacts with an equivalent amount of anhydrous nitric acid forming a liquid reaction mixture. This liquid reaction mixture is reacted with an equivalent amount of a water scavenging acid anhydride in the presence of a small amount of halide ion forming catalyst.

Shen Qiong-hua et al (28$^{th}$ International Conference of ICT, Jun. 25–28, 1996, Karlsruhe, P133-1) discloses a method of preparing butyl-NENA batchwise in a laboratory scale by the use of very small amounts of starting materials. Nitric acid is initially cooled in an ice/salt water bath, whereupon n-butyl-ethanolamine is added below the liquid surface to the acid with vigorous stirring. The temperature is kept below 22° C. After all the amine is added, the mixture is left with stirring in about 50 minutes. A mixture of acetic acid anhydride and zinc chloride is then added to the mixture at such a rate that the temperature is kept below 35° C. When the entire mixture of acetic acid and zinc chloride is added, the reaction mixture is left for about 1 hour with stirring and then poured into an ice bath. Butyl-NENA separates as a yellowish liquid in the bottom of the ice-bath. Shen Qionghua et al concluded that the optimalized reaction conditions for the preparation of butyl-NENA was a reaction temperature of below 22° C. in the first part of the reaction and a reaction of below 35° C. in the second part of the reaction. The reaction time should be about 2.5 hours. In one experiment Shen et al obtained 98.9% purity and 84% yield. In the other experiments the purity was never better than 97% when the yield was higher than 67%.

The literature does not exhaustively disclose the preparation of Alkyl-NENAs in a larger scale than 5 liters (P. A. Silver and F. Stanley. Hercules Aero-space Division, Hercules Incorporated, Allegany Ballistics Laboratory, Maryland). The total reaction time for step one of the reaction was 4.5 hours, and the addition time for the second step of the reaction was 2.5 hours. The product phase was separated and washed three times, each time having a washing time of about 1 hour per wash. Total time for the synthesis of butyl-NENA in this 5 liter flask was stated to be as much as 10 hours. No yield or purity of the product prepared by the process in a 5 liter scale is presented.

Generally the technology of nitration includes very exothermic reactions. The synthesis of Alkyl-NENAs is so far no exception. Reaction step 1, in which alkylethanol amine is added to cold nitric acid, is a very exothermic reaction. The additon of the amine must be effected below the liquid surface to avoid "spark spheres". Controlling the rate of addition, amount added and sufficient cooling of the reaction flask is thus of great importance when alkylethanolamine is added to nitric acid. It is also important that nitric acid is not allowed to enter the addition tube of the alkylethanolamine.

Formation of sparks quickly arises in the nitration acid when the alkyletha-nolamine is added, and this is not kept under control. At a larger scale (100 l, 1000 l or largers reactors) this reaction step is expected to be particularly dangerous, and extensive and well planned measures are required before such a reaction is performed.

It is disclosed in the literature that the reaction mixture from the first step should be left with stirring for about 1 hour before a second step is entered. A mixture of acetic acid anhydride is added to a halide ion forming catalyst by the addition to the reaction mixture from the first step. Also this reaction is an exother-mic reaction, but the development of heat is less drastic than in the first part of the reaction. It is disclosed in the literature that the final reaction mixture after step two should be left for about 1 hour with stirring before the reaction mixture is poured into ice water. After this mixture is discharged into ice water, the Alkyl-NENAs will separate as distinct liquid phases in the bottom of the drowning vessel (exception: methyl-NENA which will be precipitated as crystals). The product phase must be separated, and the product washed several times before it is separated and dried.

SUMMARY OF THE INVENTION

It was therefore an object of the present invention to develop a synthesis for the use at a technical scale, which compared to the disclosure of the prior art, results in higher yields, higher purity, and to a better extent complies with the problematic safety aspects when N-alkyl-nitratoethylnitramines are prepared.

Further it was an object of the invention to develop a suitable plant for accomplishing such a synthesis.

These objects are surprisingly achieved according to the present invention by a process of preparing N-alkyl-nitratoethylnitramines, in which an N-alkyl-ethanolamine is first reacted with nitric acid and then with a mixture of acetic acid anhydride and a halide ion forming catalyst in a continuous process with subsequent work-up by being fed into an ejector, in which concurrently water is injected, and from which a mixture of water and N-alkyl-nitratoethylnitramine is passed to a separator, and therein separated into product and water containing residual acid.

According to a preferred embodiment, the first reaction between N-alkyl-ethanol amine and nitric acid is performed in a first reactor as a continuous process, and the product from this reactor is transferred to a second reactor in a continuous way, in which reactor it is further reacted by the continuous addition of acetic acid anhydride and a halide ion forming catalyst.

According to another possible embodiment, both reactions are performed in one tube reactor, the alkyl-ethanolamine and nitric acid being added upstream in the reactor, whereas the acetic acid anhydride and halide ion forming catalyst is added downstream in the reactor.

Further, preferably the product from the separator is transferred continuously to a washing step with water, whereupon the water and the washed product are separated.

According to a preferred embodiment, the wash water from the washing step is continuously transferred to a buffer tank to be returned to the ejector.

As the halide ion forming catalyst zinc dichloride ($ZnCl_2$) is particularly preferably used.

As the nitric acid $\geq 97\%$ nitric acid is preferably used. Further, it is preferred that the N-alkyl-ethanolamine is added to the reactor through a distribution system.

BRIEF DESCRIPTION OF THE DRAWINGS

The single FIGURE is a schematic representation of a production plant for performing the inventive process.

DETAILED DESCRIPTION OF THE INVENTION

Particularly, it is preferred that between about 2.0 and about 3.0 mol nitric acid is added per mol N-alkyl-ethanolamine, and particularly that between about 2.5 and about 2.8 mol nitric acid is added per mol N-alkyl-ethanolamine.

It is strongly preferred that the temperature of the first reactor is kept between about 5° C. and about 23° C.

In the preparation of N-butyl-nitratoethylnitramine it is preferred that the temperature in the second reactor is kept between about 25 and about 35° C., and it is particularly preferred that the temperature of the second reactor is kept between about 28 and about 32° C.

It is particularly preferred that an N-$C_1$–$C_4$ alkyl-ethanolamine is used in the process of the present invention, and particularly that N-butyl-ethanolamine is used.

Further, the aim of the present invention is solved by a production plant for performing the process, which is accomplished by two connected reactors as described above, comprising a first reactor (4) provided with feeding means of nitric acid (1a) and a distributed feeding of N-alkyl-ethanolamine (2a) via a distribution system (13), an agitator (4a), means for internal and external cooling of the reactor (4b) and means for conveying product (4c) to another reactor (5), said reactor (5) being equipped for the feed of a mixture of acetic acid anhydride and halide ion forming catalyst (3a), an agitator (5a), means for internal and external cooling of the reactor (5b), means for conveying the final product to an ejector (5c) having injection means for water (7, 12a), transport means (6a) from the ejector to a separator (8a) for the separation of product and water containing residual acid.

According to a particularly preferred embodiment of this plant, the separator (8) has outlet means for continuous transport of product (8a) to a washing tank with water (9), and outlet means for draining water containing residual acid (8b), and the washing tank (9) has outlet means for wash water and product (9a) to a separator (10), said separator (10) having outlet means of product to storage (10a) and outlet means for wash water to a buffer tank (10b).

For an economic operation of the plant it is preferred that the buffer tank has a transport connection to the ejector (12a) for better utilisation of material and reduction of environmental strain.

By the present invention compared to the prior art, particularly an improved purity of the final product is achieved. It is obvious to the man skilled in the art that a higher purity results in an increased stability. This is particularly important in connection with energetic compounds. In addition, the performance of energetic products will be better the purer the product, provided that the side products are inert or less energetic. All energetic compounds (nitrate esters and nitramine compounds) are basically unstable, and even at room temperature a slow decomposition takes place. The decomposition velocity increases at increasing temperatures and may be catalyzed by the impurities of the product. Thus, it is also obvious that this may have an influence on the stability of propellants or explosives including Alkyl-NENAs. Further, it is obvious that presence of impurities may result in undesirable reactions with other ingredients of propellant or explosive compositions, and thus result in undesirable alterations in the properties of the final product.

A continuous production of Alkyl-NENAs, which is the subject of the present invention, further provides for an increased yield compared to the batch production.

By the present invention compared to the prior art, a large improvement is achieved with respect to the safety in the production of Alkyl-NENAs. As already mentioned, the first reaction step of the process is a very exothermic reaction. In the batch production of large amounts of Alkyl-NENAs (100 l, 1000 l, etc.) the alkyl-ethanol-amine has to be added to large amounts of concentrated nitric acid, and the risk of accidents/disasters are much higher than in the production of large amounts of Alkyl-NENAs continuously, in which—after a specific starting procedure—alkyl-ethanol-amine and concentrated nitric acid are simultaneously added into a much smaller reactor.

Another obvious advantage of the present invention is that the constant composition inside the reactor results in stable reaction conditions and the reaction composition functions as an excellent "cooling buffer". This is also for safety reasons a great advantage compared to the batch production in which small amounts of alkyl-ethanolamine is slowly added to large amounts of concentrated acid.

The consequences of an accident/disaster in the batch production will be very high compared to the consequences of an accident/disaster in the continuous production, as the volumes of the equipment units, starting materials, intermediate and final products in the production facilities are far less in a continuous production.

A continuous production of Alkyl-NENAs results in larger amounts of product in a shorter time and by using smaller equipment units than the corresponding batch production of Alkyl-NENAs. This is a very important economic aspect of the present invention. It will also involve less manual operations by the operator of the production plant. This is important both to the capacity of the plant, and not at least to the safety of the operator. Concentrated nitric acid is very aggressive, and in addition particularly butyl-NENA is vasodilating, resulting in a strong headache.

Treatment of the wastes in the production of Alkyl-NENAs will, due to the present invention, be less than in a batch production. The first washing step in the work-up of Alkyl-NENAs takes place in the continuous production. The first wash water goes into a return loop, is mixed with process water which is further mixed with the reaction mixture of the second step of the reaction. In this way an important environmental aspect is taken care of by consistently using the first wash water in the process. In addition, the loss of product is reduced.

Further benefits of the present invention will be elucidated by the following closer description of the invention.

The present invention provides a continuous process of preparing Alkyl-NENAs. The starting materials for the production of the NENA compounds are, like previously known, nitric acid, alkyl-ethanolamine and acetic acid anhydride mixed with zinc chloride.

In the following it is referred to the figure for a closer description of the invention.

In the continuous process the starting materials nitric acid and alkyl-ethanol-amine are stored separately in intermediate tanks within the production facilities ((1)=concentrated nitric acid, (2)=alkyl-ethanolamine) and mixture of acetic acid anhydride and zinc chloride is stored in a day-tank ((3)=acetic acid anhydride added zinc chloride). These day-tanks are further fed at a low liquid level from larger storage tanks outside the building. Day-tanks involve smaller amounts within the production facilities and thereby less risk of greater accidents/disasters. The continuous process is effected by a starting procedure of reactor 1(4). The starting procedure used is the process as disclosed in well-known literature of batch reactions by feeding alkyl-ethanol-amine (2) through a distribution system (13) below the liquid surface into a cooled nitric acid which is in advance charged into the reactor 1(4). The reactor 1(4) has a very high cooling capacity of absorbing the heat released in the reaction. In addition, it is important that the alkyl-ethanol-amine is added over as large an area as possible below the liquid surface of the nitric acid to evenly distribute the heat evolution in the nitric acid.

When equivalent amounts of alkyl-ethanolamine is added to the acid in the reactor 1(4), alkyl-ethanolamine (2) and nitric acid (1) are fed in equivalent amounts simultaneously to the reactor 1(4). The reaction mixture of reactor 1(4) now partly works as a "cooling buffer", the cooling capacity of the reactor 1(4) at the same time being very high. If the temperature of the reactor 1(4) under any circumstances exceeds a maximum temperature, the reactor 1(4) is automatically opened to drown the reaction composition in water tanks being located below the reactor.

When the liquid level of the reactor 1(4) has reached a desired level, the reaction composition is fed from the reactor 1(4) to the reactor 2(5). The reactor 2(5) has also its own starting procedure. Part of the mixture of acetic acid anhy-dride and zinc chloride (3) is in advance charged to the reactor 2(5). When equivalent amounts of the reaction mixture from reactor 1(4) have been added to the mixture of acetic acid anhydride and zinc chloride (3), the reaction mixture is fed from reactor 1(4), and simultaneously a mixture of acetic acid anhydride and zinc chloride (3) to the reactor 2(5).

When the liquid level in the reactor 2(5) has reached the desired level, this reaction mixture is fed into an ejector (6) together with process water (7). The amount of process water is in advance exactly calculated to achieve as high a yield as possible. Previously disclosed batch processes of preparing Alkyl-NENAs have only disclosed that the reaction mixture corresponding to the mixture of the reactor 2(5) is drowned into ice-water, and is then left for a while before decantation. In the continuous process we have found that the temperature of the process water is sufficient (ice-water is not required for separation) provided that the reaction mixture corresponding to the mixture of the reactor 2(5) is added to water with vigorous stirring/velocity through the ejector (6). When the reaction mixture from reactor 2(5) is mixed with tap-water (7), the reaction mixture now constitutes two liquid phases. The reaction mixture/liquid phases are fed to a separator 1(8). The feeding point of the separator 1(8) is calculated from the density of the two respective liquids to obtain a minimum of turbulence in the interphase between the two liquids. In this way a mixture of the two liquids can be continuously fed, and they will be continuously separated without problems. The residence time inside the separator 1(8) is calculated to 10–20 minutes, which has been found to be sufficient. In the prior art literature, in which Alkyl-NENAs have been prepared batch-wise, the liquid phases had been left for longer period of time before they were separated. The liquid volume has in addition been considerably smaller than described in the present invention. By the present invention it is, however, possible to separate larger amounts of Alkyl-NENAs in a shorter time than what was previously known. From the separator 1(8) Alkyl-NENAs is separated in the bottom of the separator, and further passed to a washing tank (9) for a first wash, and water containing residual acid is separated from the top of the separator 1(8) and brought to a collecting tank outside the production facilities (11). In the washing tank (9) equivalent amounts of Alkyl-NENAs are fed from the separator 1(8) concurrently with process water 7(12a). This is thoroughly mixed by means of the agitator in the washing tank (9) and further brought to separator 2(10). In a corresponding way as on the separator 1(8), the feeding point is calculated from the density of the two liquids to achieve a minimum of turbulence in the liquid interphase between the two liquids. From the separator 2(10) the wash water is separated to a buffer tank (12) which is connected to process water (7) to then be turned into the process via the ejector (6). The product from the separator 2(10) is drained to a barrel, and further processed batch-wise to further washing steps. To the practitioner in the field it will, however, be a simple matter to extend the continuous process to comprise also these two last washing steps in a continuous way, and this option is also an aspect of the present invention.

A closer description of the present invention will now be presented through examples of embodiments:

Example 1 shows the preparation of butyl-NENA in 10 l plant by batch-wise production (according to the prior art), whereas Example 2 shows the preparation of butyl-NENA in a 10 l plant by continuous production according to the present invention. Further, Example 3 will show a continuous process of preparing butyl-NENA in a larger production plant.

Example 4 describes the continuous process of preparing ethyl-NENA in a 10 l plant. Example 5 describes the continuous process of preparing methyl-NENA in a 10 l plant.

EXAMPLE 1

Preparation of Butyl-NENA in a 10 I Reactor, Batch

Nitric acid 99% (2912 g, 46 mol) was added to a 10 l reactor and cooled to 14° C. Butyl-ethanolamine (2077 g, 17.7 mol) was slowly added by means of nitrogen pressure below the liquid surface of the nitric acid. The stirring was maintained at about 300 rpm. The temperature was kept between 15° C.–20° C. The butyl-ethanolamine addition took about 2 hours. The mixture was left with stirring at room temperature for about 1 hour and 15 minutes. A mixture of acetic acid anhydride (5100 g, 50 mol) and a catalytic amount of zinc chloride (47.2 g, 0.35 mol) was slowly added with stirring to the reaction mixture. The temperature was kept between 30° C. and 35° C. The addition lasted for about 1 hour and 15 minutes. The mixture was left at room temperature with agitation for about 1 hour before being drained into ice-water (7 kg ice). The mixture was left at room temperature to the next day for a sufficient separation.

The residual acid/water phase was separated by decantation, the organic phase was washed three times; the first time with equal amounts of water, the second time with a 5% sodium carbonate solution and at last water once more. The butyl-NENA was separated and then dried by nitrogen bubbling for 24 hours.

| | |
|---|---|
| Theoretical yield: | 3652 g |
| Yield: | 2591 g; 71% |
| Acidity: | 0.006% |
| Purity: | 97% |
| Moisture: | 0.25% |
| DSC peak (10° C./min.) | 210° C. |

This example shows that about 48 hours were required to produce 2.5 kg butyl-NENA; final work-up.

EXAMPLE 2

Preparation of Butyl-NENA in 10 I Reactor: Continuously

Nitric acid, 99% (2955 g, 46.9 mol) was added to a 10 l reactor and cooled to 19° C. At the same time acetic acid anhydride (2550 g, 25 mol) and zinc chloride (30 g, 0.22 mol) was added to reactor 2 and the agitation was started.

Start-Up Procedure of Reactor 1

The agitation in reactor 1 was started. Butyl-ethanolamine (2066 g, 17.7 mol) was fed through a pressurized distribution system to the reactor 1 at a rate of 38.7 ml/min. The temperature was all the time monitored to not exceed 22° C. After about 1 hour the start-up procedure of the reactor 1 is completed.

Start-Up Procedure of Reactor 2 Simultaneously With Continuous Operation of Reactor 1

Butyl-ethanolamine (3099 g, 26.5 mol) and nitric acid 99% (4430 g, 70.3 mol) were simultaneously added to reactor 1 at a feed rate of 38.7 ml/min. and 328 ml/min, respectively. The intermediate product from the reactor 1 was pumped into the reactor 2, wherein the mixture of acetic acid anhydride and a catalytic amount of the zinc chloride was ready, at a rate of 71.5 ml/min. The temperature of the reactor 2 was kept below 35° C., and the temperature of the reactor 1 did not exceed 22° C. After about 30 minutes, the start-up procedure of the reactor 2 was finished.

Continuous Operation

A ready mixture of acetic acid anhydride (10200 g, 100 mol) and zinc chloride (120 g) was fed to the reactor 2 at a rate of 78.6 ml/min., simultaneously with the intermediate product from the reactor 1 (at a rate of 71.5 ml/min.).

Nitric acid and butyl-ethanolamine were now continuously pumped into the reactor 1. Simultaneously the intermediate product from the reactor 1 and mixture of acetic acid anhydride and zinc chloride was continuously pumped into the reactor 2. The feed rates are closely calculated and the temperatures were closely monitored. The reaction mixture from the reactor 2 was at a desired level added to an ice/water mixture in a given ratio by means of a siphon (about 1.3 kg reaction mixture in 11 kg ice-water).

The continuous process was run for about 2 hours before the addition of butyl-ethanolamine and nitric acid was stopped. The rest of the reaction mixture in reactor 1 was pumped into reactor 2 simultaneously adding acetic acid anhydride and zinc chloride. When reactor 1 was empty, also the continuous addition of acetic acid anhydride and zinc chloride to reactor 2 was stopped. The contents of reactor 2 was drained into the ice/water mixture, and butyl-NENA separated as a light yellowish liquid.

| | |
|---|---|
| Theoretical yield: | 9138 g |
| Yield (before washing) | about 8100 g; i.e. 88.6%. |

This example shows that it took one day of work to produce slightly more than 8 kg untreated butyl-NENA. This is at least the triple capacity compared to the batch operation of butyl-NENA.

The same procedure and amounts were run for further 6 days of work, and the untreated butyl-NENA produced by these total 7 batches were combined and subjected to work-up. However, only ⅔ of the one batch was used. Butyl-NENA was first washed in water, then in 5% sodium carbonate solution and finally the last time in water. (batch 341/98, ch. 10/98).

| | |
|---|---|
| Theoretical yield: | about 58.5 kg |
| Yield: | about 44 kg; 75% |
| Acidity: | 0.002 |
| Purity: | 99.1% |
| Moisture: | 0.14% |
| DSC (10° C./min.) | 211° C. |

The results show a purity of 99.1%. This above 2% better than butyl-NENA prepared by batch-operation, which is important with respect to both the stability and performance of butyl-NENA.

EXAMPLE 3

Preparation of butyl-NENA in a Continuous Plant With 140 l and 260 l reactors

The reference numbers in brackets refer to the figure.

Preparations

Zinc Chloride (11.1 kg, 81.4 mol) and Acetic Acid Anhydride (944.5 kg, 9.3 kmol) were mixed in a day-tank (3) and agitation was activated at 65 rpm over night (at least 2 hours are required to dissolve all the zinc chloride).

Start-Up Procedure for Reactor 1 and Partly for Reactor 2

Nitric acid, 99% (1) was pumped at a rate of 67 I/hour into reactor 1(4). After exactly 29 minutes, the addition was stopped. The agitation of the reactor 1 (4) was set to 375 rpm, and the temperature was regulated to 19° C.

The mixture of acetic acid anhydride and zinc chloride (3) was pumped at a rate of 160 I/hour into reactor 2(5) and at the same time butyl-ethanolamine (2) was pumped through a pressurized distribution system at a rate of 78 I/hour into reactor 1(4). The temperature of reactor 1(4) was continuously monitored to stay between 18° C. and 20° C.

After exactly 17.5 minutes, the addition of acetic acid anhydride and zinc chloride composition (3) into reactor 2(5) was stopped. The addition of butyl-ethanolamine (2) for the start-up procedure of reactor 1(4) was finished after exactly 29 minutes.

Start-Up Procedure Reactor 2(5) and Continuous Operation of Reactor 1(4)

After 29 minutes butyl-ethanolamine (2) and nitric acid, 99% (1) were added concurrently to reactor 1(4) at a rate of 78 I/hour and 67 I/hour respectively. The temperature of the reactor 1(4) was consistently monitored to stay between 18° C. and 22° C. The agitation of reactor 2(5) was set to 300 rpm and the temperature was regulated to 30° C.

After 15 minutes continuous addition of nitric acid, 99% (1) and butyl etha-nolamine (2) an intermediate product stream from reactor 1 to reactor 2 was observed. This stream was maintained for 17.5 minutes, the temperature of reactor 2(5) being maintained between 28° C. and 32° C.

Full Continuous Operation: Continuous Addition of All Three Reactants

A mixture of acetic acid anhydride and zinc chloride (3) was now added to reactor 2(5) at a rate of 160 I/hour at the same time as intermediate product was added from reactor 1(4) to reactor 2(5). The temperatures of the reactors were maintained between 18° C. and 22° C. in the reactor 1(4) and between 28° C. and 32° C. in the reactor 2(5).

After about 20 minutes, a stream from the reactor 2(5) and towards the ejector (6) was observed. An addition of process water (7) was then started at a rate of 810 kg/hour (810 I/hour). The reaction mixture from the reactor 2(5) mixed with water flowed into the separator 1(8) in which phases separated after about 10 minutes. The process water (7) fed into the washing tank was set to 105 kg/hour when a product stream was observed from the separator 1(8) to the washing tank (9). The wash water and the product flowed into the separator 2(10) and the butyl-NENA (light yellowish liquid) was then drained to a barrel from the separator 2(10). After 144 minutes of continuous operation, the plant was closed and drained. Draining the plant required 140 minutes.

| | |
|---|---|
| Theoretical yield: | 669 kg |
| Yield: | About 545 kg; 81.5% (after first wash). |

Butyl-NENA was washed once with 5% sodium carbonate solution and finally once with water before drying.

| Yield:            | 490.5 kg; 73.3% |
| ----------------- | --------------- |
| Acidity:          | 0.001%          |
| Purity:           | 99.5%           |
| Moisture:         | 0.037%          |
| DSC (10° C./min.) | 280° C.         |

This example indicates that butyl-NENA is produced at a purity of 99.5%. This is a superior purity of the specific product and is far better than what was known to be obtained with the production of butyl-NENA in a batch-plant. This result is also better than presented in Shen et al. for the production of butyl-NENA in laboratory scale.

In addition, the example indicates that 490 kg product has been produced in two days with reactors being no larger than 140 I and 260 I.

The preparation of butyl-NENA as indicated in Example 3 is performed in a plant (see the figure) having a capacity of above 100 kg/hour. The plant is, of course, able to be run continuously over several days when required. In this way it will have a capacity of producing Alkyl-NENAs which is very high.

EXAMPLE 4

Preparation of Ethyl-NENA in 10 I Reactor: Continuously

99% nitric acid (2835 g, 45.0 mol) was added to a 10 I reactor and cooled to 19° C. Concurrently acetic acid anhydride (2288 g, 22.4 mol) and zinc chloride (30 g, 0.22 mol) was added to the reactor 2 and the agitator was started.

Starting Procedure Reactor 1

The agitator of the reactor 1 was started. Ethyl-ethanolamine (1780 g, 20 mol) was fed through a pressurized distribution system to the reactor 1 at a rate of 32.5 ml/min. The temperature was all the time monitored not to exceed 9° C. After about 1 hour the starting procedure of the reactor 1 is finished.

Starting Procedure Reactor 2 Simultaneously With Continuous Operation of Reactor 1

Ethyl-ethanolamine (3560 g, 40.0 mol) and nitric acid, 99% (5670 g, 90.0 mol) was concurrently added to the reactor 1 with feed rates of 32.5 ml/min. and 31.5 ml/min. respectively. The intermediate product from the reactor 1 was pumped into the reactor 2, in which the mixture of acetic acid anhydride and a catalytic amount of zinc chloride was completed, at a rate of 64.0 ml/min. The temperature of the reactor 2 was kept below 35° C., and the temperature of the reactor 1 did not exceed 9° C. After about 30 minutes, the starting procedure of the reactor 2 was completed.

All Continuous Operation

A ready mixture of acetic acid anhydride (11437 g, 112.1 mol) and zinc chloride (150 g) was fed to the reactor 2 at a rate of 70.5 ml/min. concurrently with the intermediate product from the reactor 1 (at a rate of 64.0 ml/min.).

Nitric acid and ethyl-ethanolamine were now pumped into the reactor 1. Simultaneously intermediate product from the reactor 1 and the mixture of acetic acid anhydride and zinc chloride was continuously pumped into the reactor 2. The feed rates are closely calculated, and the temperatures were closely monitored. The reaction mixture of the reactor 2 was at a desired level added to an ice/water mixture in a given ratio by means of a siphon (about 1.3 kg reaction mixture in 11 kg ice water).

The continuous process was run for about 1 hour and 40 minutes, before the addition of ethyl-ethanolamine and concentrated nitric acid was stopped. The remaining reaction mixture of the reactor 1 was pumped into the reactor 2 simultaneously with the addition of acetic acid anhydride and zinc chloride. When the reactor 1 was empty, also the continuous addition of acetic acid anhydride and zinc chloride to reactor 2 was stopped. The contents of the reactor 2 was drained into the ice/water mixture, and ethyl-NENA precipitated as a light yellowish liquid.

| Theoretical yield:   | 10740 g                     |
| -------------------- | --------------------------- |
| Yield (before wash): | about 9000 g; i.e. 83.7%.   |

This example illustrates that it took one day of work to produce about 8 kg non-processed ethyl-NENA.

EXAMPLE 5

Preparation of Methyl-NENA in 10 I Reactor: Continuously

Nitric acid, 99% (2835 g, 45.0 mol) was added to a 10 I reactor and cooled to 19° C. Acetic acid anhydride (2228 g, 22.4 mol) and zinc chloride (30 g, 0.22 mol) were concurrently added to the reactor 2 and the agitator was started.

Starting Procedure of Reactor 1

The agitator of reactor 1 was started. Methyl-ethanolamine (1500 g, 20 mol) was fed through a gas pressurized distribution system to the reactor 1 at a rate of 26.6 ml/min. It was all the time monitored that the temperature did not exceed 9° C. After about 1 hour, the starting procedure of reactor 1 is complete.

Starting Procedure of Reactor 2 With Simultaneously Continuous Operation of Reactor 2.

Methyl-ethanolamine (3000 g, 40.0 mol) and nitric acid, 99% (5670 g, 90.0 mol) were added concurrently to the reactor 1 at a feed rate of 26.6 ml/min. and 31.5 ml/min. respectively. The intermediate product from the reactor 1 was pumped into the reactor 2, in which the mixture of the acetic acid anhydride and a catalytic amount of zinc chloride was ready mixed, at a rate of 58.1 ml/min. The temperature of the reactor 2 was kept below 35° C., and the temperature of the reactor 1 did not exceed 9° C. After about 30 minutes, the starting procedure of the reactor 2 was complete.

All Continuous Operation

A ready mixture of acetic acid anhydride (11437 g, 112.1 mol) and zinc chloride (150 g) was fed to the reactor 2 at a rate of 70.5 ml/min., concurrently with he intermediate product from the reactor 1 (at a rate of 58.1 ml/min.).

Nitric acid and methyl ethanol amine were now continuously pumped into the reactor 1. At the same time the intermediate product from the reactor 1 and a mixture of actic acid anhydride and zinc chloride was continuously pumped into the reactor 2. The feed rates are closely calculated, and the temperatures were closely monitored. The reaction mixture of the reactor 2 was added at a desired level to an ice/water mixture in a given ratio by means of a siphon (about 1.3 kg reaction mixture in 11 kg ice-water).

The continuous process was run for about 2.5 hours, before the addition of methyl-ethanolamine and concentrated nitric acid was stopped. The rest of the reaction mixture of the reactor 1 was pumped into the reactor 2 concurrently with addition of acetic acid anhydride and zinc chloride. When the reactor 1 was empty, also the continuous addition of acetic acid anhydride and zinc chloride to the reactor 2 was stopped. The contents of the reactor 2 was drained into the ice/water mixture and methyl-NENA precipitated as white crystals.

| | |
|---|---|
| Theoretical yield: | 9900 g |
| Yield (before washing) | about 7.6 kg; 76.8%. |

It must be emphasized that the examples above are only presented to elucidate the present invention, and that a man skilled in the art will be able to make variations of the features described therein within his general professional knowledge. Such variations must thus be considered to be within the scope of the present invention as defined by the appending patent claims.

What is claimed is:

1. A process of preparing N-alkyl-nitratoethylnitramines, comprising at first reaction of a N-alkyl-ethanolamine with nitric acid and subsequently with a mixture of acetic acid anhydride and a halide ion forming catalyst in a continuous process with subsequent work-up by introduction into an ejector, into which water is concurrently injected, and from which the mixture of water and N-alkyl-nitratoethylnitramine is passed to a separator, and therein separated into product and water containing residual acid.

2. The process of claim 1, wherein the first reaction between N-alkyl-ethanol-amine and nitric acid is carried out in a first reactor as a continuous process, and the product from said reactor is transferred to another reactor in a continuous way, in which reactor it is further reacted by continuous addition of a mixture of acetic acid anhydride and a halide ion forming catalyst.

3. The process of claim 1, wherein both reactions are carried out in one single tube reactor, the alkyl ethanol amine and nitric acid being added upstream in the reactor, whereas acetic acid anhydride and halide ion forming catalyst are added downstream in the reactor.

4. The process of claim 1, wherein the product from the separator is continuously transferred to a washing step with water, whereupon the water and the washed product are separated.

5. The process of claim 1, wherein the wash water from the washing step is continuously transferred to a buffer tank for return to the ejector.

6. The process of claim 1, wherein the halide ion forming catalyst is zinc dichloride ($ZnCl_2$).

7. The process of claim 1, wherein $\geq 97\%$ nitric acid is used.

8. The process of claim 1, wherein the N-alkyl-ethanolamine is added to the reactor through a pressurized distribution system.

9. The process of claim 1, where in the reaction is added between about 2.0 and about 3.0 mol nitric acid per mol N-alkyl-ethanolamine.

10. The process of claim 9, where in the reaction is added between about 2.5 and about 2.8 mol nitric acid per mol N-alkyl-ethanolamine.

11. The process of claim 2, wherein the temperature of the first reactor is kept between about 5° C. and about 23° C.

12. The process of claim 2, wherein the temperature of the second reactor is kept between about 25 and about 35° C.

13. The process of claim 12, wherein the temperature of the second reactor is kept between about 28 and 32° C.

14. The process of claim 1, wherein the N-alkyl-ethanolamine is an N-$C_1$–$C_4$ alkyl-ethanolamine.

15. The process of claim 14, wherein the N–$C_1$–$C_4$ alkyl-ethanolamine is N-butyl-ethanolamine.

* * * * *